United States Patent [19]

Inouye et al.

[11] 4,076,588

[45] Feb. 28, 1978

[54] ANTIBIOTIC SF-1623 SUBSTANCE AND THE PRODUCTION THEREOF

[75] Inventors: Shigeharu Inouye; Takashi Shomura, both of Yokohama; Michio Kojima, Tokyo; Yasuaki Ogawa, Yokohama; Hiroshi Watanabe, Yokohama; Yasumitsu Kondo, Yokohama, all of Japan; Kazuo Saito, deceased, late of Fujisawa, Japan, by Nobuko Saito, administrator; Yujiro Yamada; Taro Niida, both of Yokohama, Japan

[73] Assignee: Meiji Seika Kaisha, Ltd., Tokyo, Japan

[21] Appl. No.: 703,589

[22] Filed: Jul. 8, 1976

Related U.S. Application Data

[62] Division of Ser. No. 526,731, Nov. 25, 1974, Pat. No. 4,010,155.

[30] Foreign Application Priority Data

Nov. 28, 1973 Japan .................................. 48-132594

[51] Int. Cl.$^2$ ................................................ C12D 9/14
[52] U.S. Cl. ................................. 195/36 C; 195/80 R
[58] Field of Search .............. 195/80 R, 36 P, 36 C; 260/243 C

[56] References Cited

U.S. PATENT DOCUMENTS

| 3,219,663 | 11/1965 | Demain ........................... 260/243 C |
| 3,914,157 | 10/1975 | Stapley et al. .................... 195/80 R |

*Primary Examiner*—Alvin E. Tanenholtz
*Assistant Examiner*—Robert J. Warden
*Attorney, Agent, or Firm*—Larson, Taylor and Hinds

[57] ABSTRACT

A new antibiotic designated as SF-1623 substance exhibiting a useful antibacterial activity against gram-negative bacteria is now produced by cultivating a new strain ATCC 21999 of the known species *Streptomyces chartreusis*. The SF-1623 substance in the form of its an alkali metal salt may be recovered from the culture when the cultivation is effected under aerobic conditions in the presence of an alkali metal thiosulfate.

4 Claims, 2 Drawing Figures

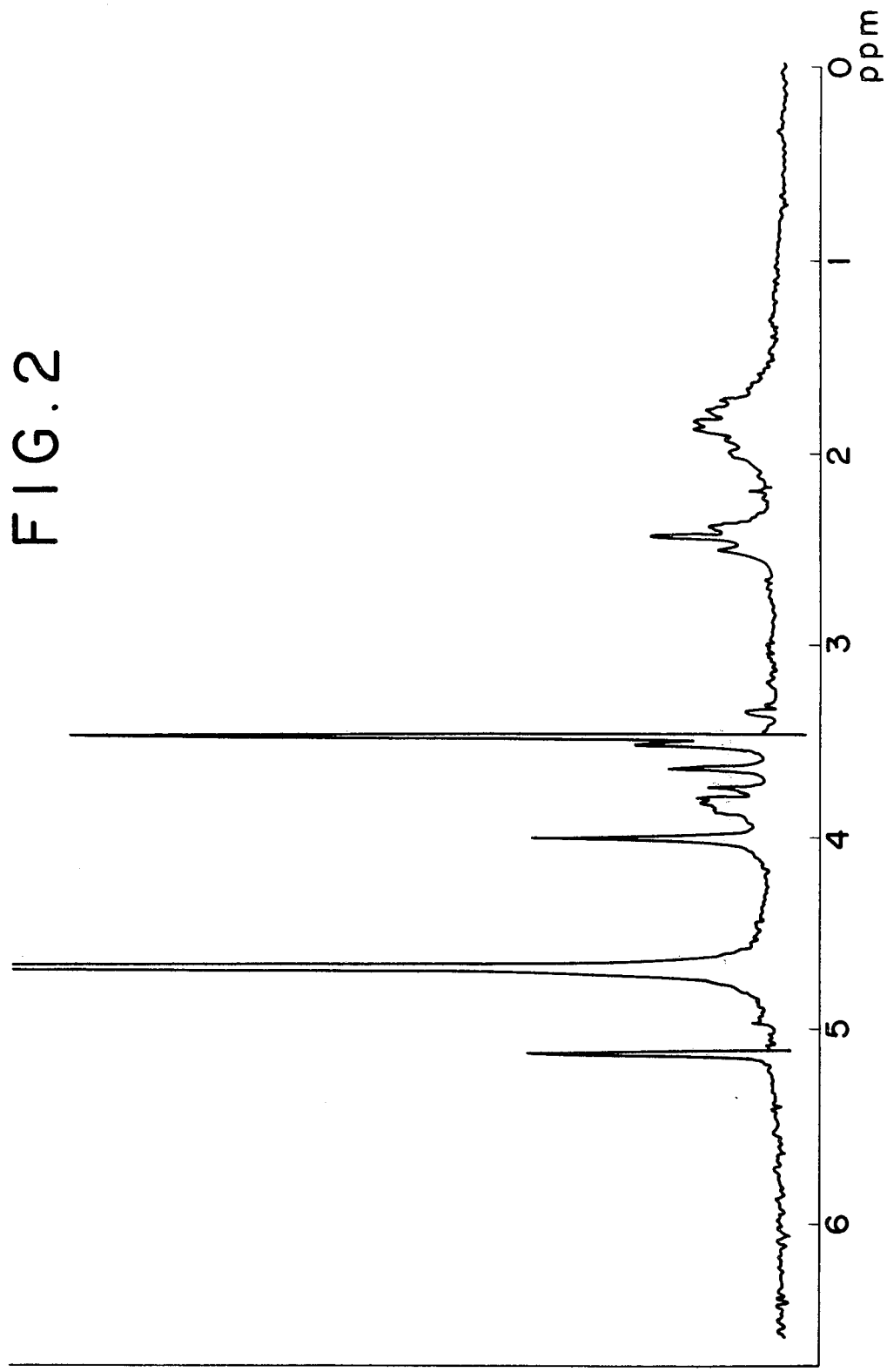

ANTIBIOTIC SF-1623 SUBSTANCE AND THE PRODUCTION THEREOF

This is a division of application Ser. No. 526,731 filed Nov. 25, 1974, now U.S. Pat. No. 4,010,155.

This invention relates to a new antibiotic SF-1623 substance which exhibits a useful antibacterial activity mainly against gram-negative bacteria. This invention further relates to a process for the production of the SF-1623 substance by cultivating a microorganism which belongs to a strain of the genus Streptomyces.

We have mad extensive research in an attempt to produce new and useful antibiotics. As a result, we have now found that when a strain of the genus Streptomyces which was isolated from a soil sample collected in Shimane Prefecture, Japan is cultivated in a culture medium under aerobid conditions, a substance which exhibits an antibacterial activity mainly against gram-negative bacteria is produced and accumulated in the culture. We have now succeeded in isolating this antibacterial substance from the culture and purifying it. As a result of the examination of the chemical, physical and biological properties of this isolated substance, we have now confirmed that this substance is a new antibiotic which is distinguishable from any of the known antibiotics. Thus, we have designated this new antibiotic as SF-1623 substance. Our further investigation of this new substance have revealed that SF-1623 substance has the following chemical structure:

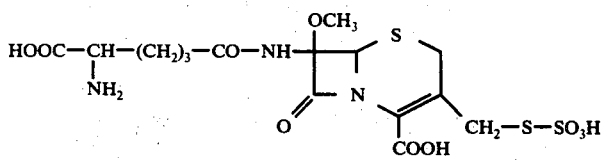

According to the first aspect of this invention, therefore, there are provided as a new and useful compound the SF-1623 substance of the formula:

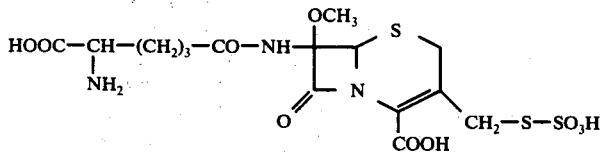

and its non-toxic, pharmaceutically acceptable salts. These salts may be in the form of a carboxylatethiosulfate with a non-toxic cation such as sodium, potassium, lithium cation, including ammonium cation, as well as an alkaline earth metal cation such as calcium and magnesium cation. An alkali metal salt, including the ammonium salt, of the SF-1623 substance is represented by the formula:

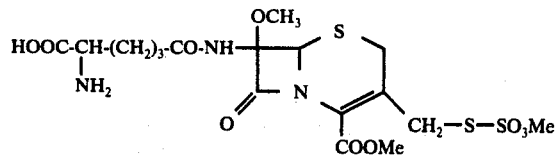

wherein Me is an alkali metal cation such as sodium or potassium cation, or ammonium cation. The SF-1623 substance (the free acid form) may also form an acid-addition salt with an organic base such as amine. The amine which may constitute such acid-addition salt with the free acid form of the SF-1623 substance of this invention may be, for example, a mono-alkyl amine such as ethylamine, isopropylamine, n-butylamine, isobutylamine and ethylenediamine; a di-alkylamine such as diethylamine, di-n-butylamine, di-iso-butylamine; a tertiary alkyl amine such as trimethylamine, triethylamine; an arylamine such as benzylamine and tribenzylamine and a heterocyclic amine such as morpholine and piperidine.

Referring to the accompanying drawings:

FIG. 2 shows a nuclear magnetic resonance absorption spectrum of the sodium salt of the SF-1623 substance in deuterium oxide as measured at 100 M Hz.

Figure 1:
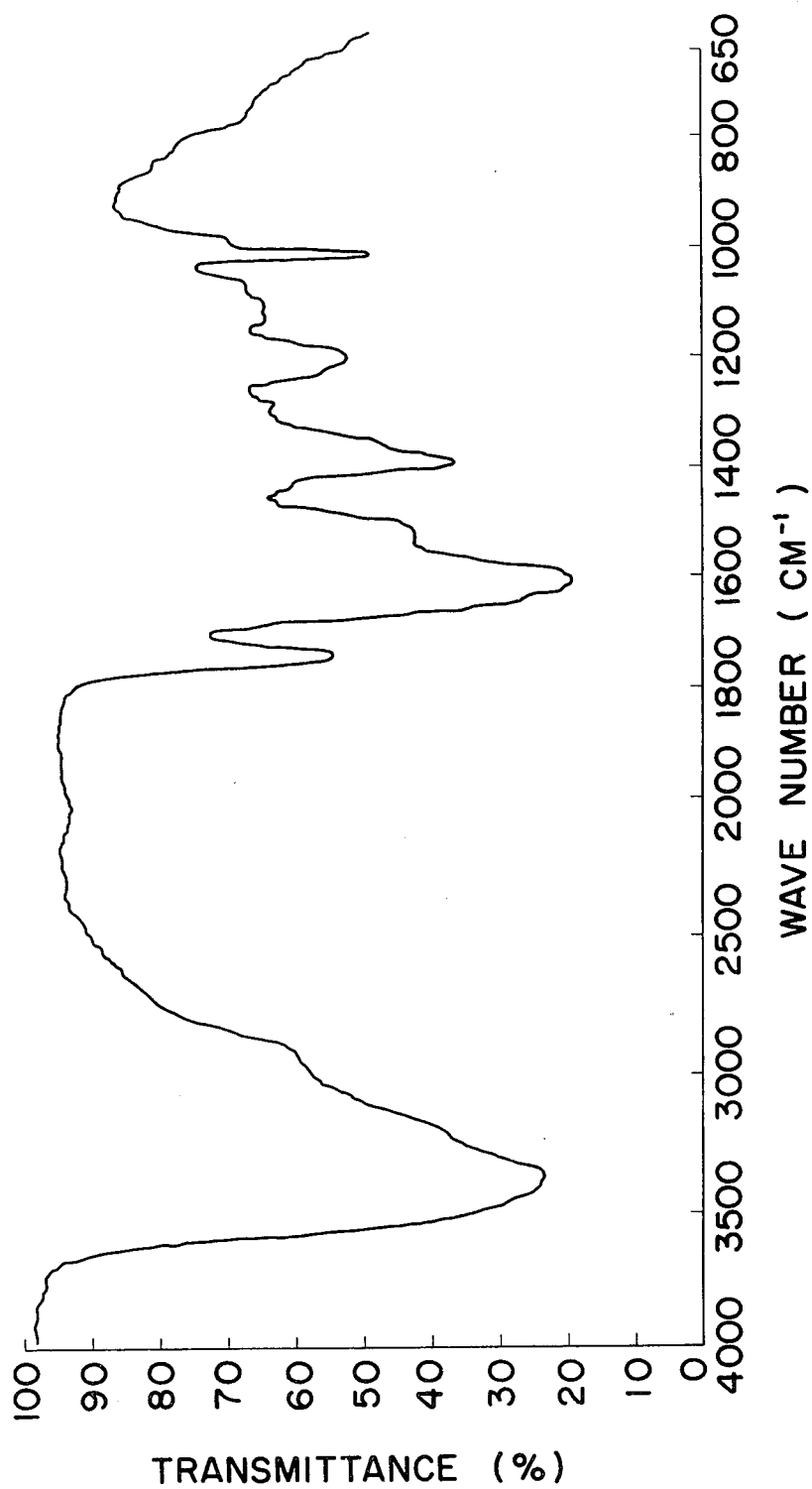
FIG. 1 shows an infrared absorption spectrum of the sodium salt of the SF-1623 substance pelleted in potassium bromide.

The SF-1623 substance (the free acid form) of this invention has the following properties: This substance is a pale yellow powder soluble in water, of the acidic nature and relatively unstable above 50° C. This substance can form a salt with a metal cation such as alkali metal cation, for example, sodium ion, potassium ion, lithium ion; ammonium ion, an alkaline earth metal ion such as calcium ion and magnesium ion. The sodium salt (the carboxylatethiosulfate form) of the SF-1623 substance represented by the formula:

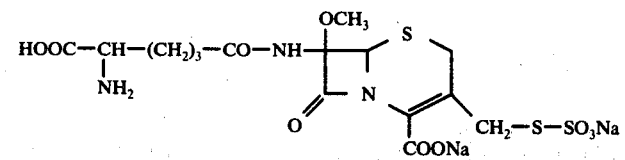

exhibits the following physical and chemical properties:
1. Appearance: A colorless powder.
2. Melting point: A clear melting point is not shown. The sodium salt is moistened in appearance in the vicinity of 140° C, then discolored slowly into a formula:

brown color and finally decomposed at 160°–165° C.
3. Solubility in solvents: Readily soluble in water but sparingly soluble in common organic solvents.
4. Specific rotation: $[\alpha]_D^{20} = +36°$ (c.1.o, $H_2O$).
5. Ultra-violet absorption spectrum: An aqueous solution of the sodium salt of the SF-1623 substance shows an absorption peak at 266 nm ($E_{1\ cm}^{1\%} = 165$).
6. Infra-red absorption spectrum: The spectrum curve is shown in FIG. 1 (pelleted in potassium bromide). A band at 1750 cm$^{-1}$ is assigned to β-lactam and bands at 1210 and 1025 cm$^{-1}$ to thiousulfate group.
7. Color reaction: Positive to the reaction with iodine, the reaction with ninhydrin and the reaction with potassium permanganate.
8. Elemental analysis: Found: C 37.62; H, 4.56; N, 7.36; O, 35.25; S, 10.67%
9. Molecular weight and natures of the elements present in the molecule: Molecular weight,550 as determined by the titration method. The elements are carbon, hydrogen, nitrogen, oxygen, sulfur and sodium.
10. Rf value: In a silica gel thin layer chromatography using "Kiesel Gel" $F_{254}$ (a product of Merck Company, Germany) as the silica gel, a single spot appears at RF 0.17 when developed with n-butanol-acetic acid-water (2:1:1) and at Rf 0.50 when developed with n-butanol-acetic acid-methanol-10% aqueous ammonium acetate-water (8:2:2:1:4). In a thin layer chromatography using aluminum sheet-cellulose (a product of Merck Company, Germany) as the thin layer, a single spot appears at Rf 0.33 when developed with n-butanol-acetic acid-water (2:1:1).
11. Neuclear magnetic resonance spectrum: The spectrum curve measured in solution in deuterium oxide at 100 MHz is shown in FIG. 2. A characteristic peak at δ 4.02 of two proton intensity is assigned to methylene attached to the thiosulfate group.
12. Stability: Stable in an acidic or neutral medium but less stable in an alkaline medium.

It is possible that the SF-1623 substance of this invention forms not only the sodium salt but also the potassium salt, lithium salt, calcium salt, magnesium salt and the ammonium salt as well as a salt with an organic amine.

Further characterization of the SF-1623 substance can be made by the conversion to its N-acyl derivatives, for example, N-ethoxycarbonyl derivatives, which is prepared by treating the SF-1623 substance with ethoxycarbonyl chloride in aqueous solution by the well-known procedure of N-ethoxycarbonylation of amino acid.

Sodium salt of N-ethoxycarbonyl-SF-1623 substance shows m.p. 180° C (decomp.), $[\alpha]_D^{20} + 46°$ (c = 1.0, $H_2O$), UV(λmax, $E_{1\ cm}^{1\%}$)241nm(105), 269(140) ($H_2O$)

Elemental analysis Cald. for $C_{18}H_{22}N_3O_{12}S_3Na_3$: C, 34.0; H, 3.5; N, 6.6; S, 15.1%. Found: C, 34.47; H, 4.39; N, 6.31%.

The SF-1623 substance of this invention exhibits an antibacterial spectrum as shown in the following Table 1. The minimum inhibitory concentrations (M.I.C.) of the SF-1623 substance (sodium salt) against various microorganisms as shown in the following table were determined according to a known broth dilution method in such a manner that the determination was effected after the incubation was effected for 24 hours at 37° C with such various incubation medium as identified below.

TABLE 1

Antibacterial spectrum of the SF-1623 substance (sodium salt)

| Test Microorganism | M.I.C. (mcg/ml) | Incubation medium |
|---|---|---|
| *Vibrio percolans* ATCC 8461 | 0.39 | 1 |
| *Alcaligenes faecalis* ATCC 8750 | 6.25 | 1 |
| *Proteus vulgaris* | 25 | 1 |
| *Escherichia coli* | 100 | 1 |
| *Salmonella typhi* | 3.12 | 1 |
| *Xanthomonas oryzae* | 50 | 2 |
| *Micrococcus lysodiekticus* | 25 | 1 |
| *Bacillus stearothermophilus* | 25 | 3 |
| *Bacillus subtilis* 6633 | >200 | 1 |
| *Staphylococcus aureus* 209P | >200 | 1 |

In the above table: Incubation medium 1 denotes a bouillon medium; 2 denotes a sodium gulutamate medium; 3 denotes a glucose-tryptone.

From the above Table 1, it is clear that the SF-1623 substance of this invention exhibits a high antibacterial activity mainly to gram-negative bacteria. In view of the above-mentioned physical and chemical properties and the antibacterial spectrum of the SF-1623 substance, it is confirmed that the SF-1623 substance does not coincide with any of the known antibiotics and is a new antibiotic.

From the results of test for acute toxicity-by intravenous administration, it has been found that the SF-1623 substance of this invention is of low toxicity. Thus, when its sodium salt was injected intravenously to mice, all mice survived at the doses of 100 mg/kg and 200 mg/kg.

The SF-1623 substance of this invention may be produced by cultivating a strain of *Strentemyces chartreusis* under aerobic conditions in the same manner as in the production of known antibiotics which is usually carried out by the cultivation of known strains of the genus Streptomyces. According to a second aspect of this invention, therefore, there is provided a process for the production of an alkali metal salt of the SF-1623 substance, which comprises cultivating an SF-1623 substance-producing strain of *Steptomyces chartreusis* in a culture medium containing assimilable nitrogen and carbon sources in the presence of an alkali metal thiusulfate under aerobic conditions to produce and accumulate the alkali metal salt of the SF-1623 substance in the culture and then recovering the resulting salt form of the antibiotic substance from the culture.

As an example of a strain of *Streptomyces chartreusis* which produces the SF-1623 substance of this invention is mentioned such a strain which we firstly isolated from a soil sample collected in Shimane-Prefecture, Japan and we have designated as *Streptomyces chartreusis* SF-1623.

The strain *Streptomyces chartreusis* SF-1623 has the following characteristics:

I. Morphological Observation

Aerial mycelia are abundantly produced on starch-agar, yeast-malt-agar and oat meal-arar, and the formation of spores is abundant.

The mycelium produces monopodially branches but does not produce whorl. The aerial mycelium bears spirals (mainly open spirals) at the tip thereof. No formation of such special structure as selerotium is observed. Electron-microscopic observation shows that the surface structure of the spore is spiny. The spores are of elliptical shape to oval shape and are normally measuring 0.5–0.8 microns by 0.8–1.0 micron in size. Mature spore chains with move than 10 spores per chain are usually produced.

II. Cultural characteristics on different culture media are shown in Table 2 below.

TABLE 2

| Culture medium | Growth (Color of the reverse side) | Aerial mycelium | Soluble pigment |
|---|---|---|---|
| Sucrose nitrate agar | Faintly yellowish brown to yellowish brown | White in greyish white | Faintly amber, unaffected by the pH |
| Glucose asparagine agar | Cream to faintly yellowish brown | Scant, white | None |
| Glycerine asparagine agar | Yellowish cream | Scant, white | None |
| Starch agar | Good, yellowish brown | Abundant, greyish blue to greenish blue | None |
| Oat meal agar | Good, yellowish cream | Abundant, bluish grey | None |
| Yeast malt agar | Good, deep brown | Abundant greyish blue to greenish blue | Brown, unaffected by the pH |
| Nutrient agar | Poor, colorless | None | None |
| Tyrosine agar | Good, dark brown to black | Abundant, greyish blue | Brown, unaffected by the pH |
| Potato plug | Raised, yellowish brown | White | None |

Note: The incubation temperature was 28° C in general, unless stated otherwise.

III. Physiological Properties
1. Growth temperature range: The strain SF-1623 grows in a temperature range of 10°–42° C on the yeast-malt-agar medium.
2. Liquefaction of gelatine: Gelatine is slightly liquefied by the incubation at 20° C for 30 days.
3. Hydrolysis of starch: Positive (intense at 28° C).
4. Coagulation of skimmed milk: Positive at 37° C but negative at 28° C.
5. Peptonization of skimmed milk: Positive at 37° C and also at 28° C.
6. Chromogenicity: Positive IV. Utilization of carbon sources (estimated in Pridham-Gottieb's agar medium)
D-glucose, D-fructose, D-mannitol, D-xylose, L-arabinose, I-inositol, rhamnose, sucrose and raffinose are all utilized for growth.

The above-mentioned characteristics of the strain SF-1623 may be summarised as follows: the aerial mycelium produces spirals (open) and the surface structure of the spore is spiny. The color of the reverse side of the growth is cream to yellowish brown to brown and is not tinged distinctively. The aerial mycelium is greyish blue to greeenish blue in color. On organic culture media, the formation of melanine-like pigment of brown color is observed. Formation of any soluble pigment other than the melanine-like pigment is scarcely observed. On the sucrose-nitrate medium, however, there is formed pigment of light amber color which is unaffected by the pH.

In view of the description of I.S.P. (International Streptomyces Project) in which reference is made to the articles of the "International Journal of Systematic Bacteriology" Vol. 18, pages 69–189 and 279–392 (1968); Vol. 19, pages 391–512 (1969) and Vol. 22 pages 265–394 (1972)), as well as in view of Bennett's description (W. H. Trejo & R. E. Bennett: the "Journal of Bacteriology" Vol. 85, pages 676–690 (1963), it has been found that the strain SF-1623 is closest to the known species Streptomyces chartreusis among the various microorganisms which appear to be analogous to the strain SF-1623.

Thus, the strain SF-1623 coincides with the known species Streptomyces chartreusis entirely not only in respect to the formation of spirals and spiny spore, the formation of aerial mycelium of bluish color and the formation of melanine-like pigment as the characteristics of these two species but also in respect to the color of the growth and utilization of sugars. When the comparison is made in more detail, it is seen that they are differentiated from each other in that the strain SF-1623 produces a soluble pigment of amber color on the sucrose-nitrate medium and a soluble pigment of brown color on the tyrosine medium, whereas the known species Streptomyces chartreusis does not produce any soluble pigment on these two media.

In consequence, it is reasonable that the strain SF-1623 is identified as a strain of the known species Streptomyces chartreusis, because they are well concident with each other in respect to their basic characteristics, though some differences may be observed between them. Accordingly, we have designated the strain SF-1623 as Streptomyces chartreusis SF-1623 in order to make the SF-1623 strain distinguishable from the known strains of Streptomyces chartreusis. This strain SF-1623 has been deposited in a Japanese public depository "Fermentation Research Institute", Chiba-city, Japan under a deposition number FERM-P No. 2348 (a culture of this strain was received by F.R.I. on 5th November, 1973) and also in the American Type Culture Collection, Washington D.C., U.S.A., under ATCC number 2199.

The strain SF-1623 has properties which are liable to vary as may usually be observed with the other species of Streptomyces. Thus, for example, the strain SF-1623 may produce a variant or mutant when it is treated with various mutagens such as ultra-violet radiations, X-rays, radio-active rays, high-frequency electromagnetic waves and chemicals. Any natural or artifical variant or mutant of the SF-1623 strain may be used for the production of the SF-1623 substance according to the concept of this invention, as long as it has the ability to produce the SF-1623 substance of this invention.

In the process of this invention, an SF-1623 substance-producing, strain of Stretomyces chartreusis and particularly the strain SF-1623 (ATCC 21999) may be cultivated in a known manner under aerobic conditions in a culture medium containing nutrients, namely such carbon and nitrogen sources which are assimilable by ordinary microorganisms. As the nutrient sources may be employed any of the known nutrient substances which have commonly been employed in the cultivation of the known strains of Streptomyces. For instance, glucose, starch, glycerine, sucrose, starch syrup, molasses, soybean oil and the like are useful as the carbon source. Further, soybean meal, wheat-embryo, meat extract, peptone, dried yeast, corn steep liquor, soluble vegetable protein, ammonium sulfate, sodium nitrate and the like may be used as the nitrogen source. If required, inorganic salts such as calcium carbonate, sodium chloride, potassium chloride, iron sulfate, nickel chloride, phosphates and the like may be added to the culture medium. In addition, to the culture medium may be added such organic and inorganic materials which aid the growth of the strain SF-1623 and promote the production of the SF-1623 substance.

An alkali metal thiosulfate such as sodium thiosulfate and potassium thiosulfate, including ammonium thiosulfate, should be present initially in the culture medium and or added subsequently to the culture broth during the cultivation, to ensure the production of the alkali metal salt of the SF-1623 substance. It is suitable that the total amount of the alkali metal thiosulfate present in or added to the culture medium is at least 0.05% by weight of the culture medium. Optimum concentration of the alkali metal thiosulfate may be determined by preliminary tests.

As the method of cultivating the SF-1623 substance-producing strain, liquid cultivation methods and particularly liquid cultivation method under submerged aerobic conditions are most preferred similar to the general processes of the production of the known antibiotics. The cultivation may suitably be effected under aerobic conditions and the suitable incubation temperature is in a range of 28° C to 37° C. For the commercial or laboratory production of the SF-1623 substance, however, it is often preferred to carry out the cultivation at a temperature in the vicinity of 28° C. In these circumstances, the concentration of the SF-1623 substance in the culture broth reaches a maximum at the end of 2 to 6 days of fermentation, either in shake-cultivation methods or in tank-cultivation methods.

For assay of the SF-1623 substance of this invention, the following method may be used: the assaying culture medium comprising 1.0% polypeptone, 0.5% meat extract, 0.5% sodium chloride and 2.0% agar (pH 7.0) is used. As the assaying microorganism is used *Vibrio percolans* ATCC 8461. In this assaying method, at a concentration of 25.0 meg/ml to 200 meg/ml of the SF-1623 substance, the relation between the logarithm of the concentration and the diameter of the inhibition zone can be plotted lineraly, giving the inhibition zone of 13.0 mm to 24.3 mm in diameter (as determined by the paper-disc method).

As the SF-1623 substance (the alkali metal salt) is a water-soluble substance as stated hereinbefore, it may be recovered from the culture broth by adsorbing on an anion-exchange resin such as Amberlite IRA-68 (a product of Rohm & Haas Co., U.S.A., an anion-exchange resin consisting of a polystyrene containing amine groups as the functional group) and Dowex 1 × 2 (a product of Dow Chemical Co., U.S.A., an anion-exchange resin consisting of a styrene-divinylbenzene copolymer containing quarternary ammonium hydroxide groups as the functional group), and then eluting from the resin by means of an aqueous solution of a suitable salt.

For the recovery of the SF-1623 substance in the form of its sodium salt from the culture broth, for example, it is efficient to pass the culture broth filtrate through a column of a resin of Amberlite IRA-68 (Cl-cycle), allow the antibiotic substance to be adsorbed by the resin, wash the resin column with water and then effect the elution with aqueous sodium chloride. In this way, a crude product of the sodium salt of the SF-1623 substance may be obtained, which may further be purified chromatographically using active carbon, cellulose, silica gel, alumina, dextran gel cross-linked with epichlorohydrin or other molecular sieve such as DEAE-Sephades (a product of Pharmacia Co., Sweden which is an anion-exchange molecular sieve consisting of a dextran gel containing diethylamino groups as the basic function) and Sephadex G-10 (a product of Pharmacia Co., Sweden, which is a molecular sieve consisting of a dextran gel), so that a pure product of the SF-1623 substance in the form of its sodium salt may be isolated as a colorless powder.

The SF-1623 substance of this invention is valuable as an antibacterial agent or therapeutic agent in poultry and animals, including man, and is especially valuable in the treatment of infectious diseases caused by gram-negative bacteria. The new antibiotic of this invention is expected to be usefully employed for such infectious diseases by topical application or parenteral administration.

According to a further aspect of this invention, therefore, there is provided a method of treating infections caused by gram-negative bacteria, which comprising administrating an effective dose of the SF-1623 substance or its non-toxic pharmaceutically acceptable salt to the infected host. Examples of the non-toxic pharmaceutically acceptable salt of the SF-1623 substance include the sodium salt, potassium salt, ammonium salt, calcium salt, magnesium salt and the like.

Just like to cephalosperin C, a known antibiotie, the SF-1623 substance of this inveention is also useful as a starting material or an intermediate product for the production of new semi-synthetic cephalosporin derivatives.

This invention is now illustrated with reference to the following Examples to which this invention is not limited.

EXAMPLE 1

A loopful quantity of spores of *Streptomyces chartreusis* SF-1623 (identified as ATCC 2199) was inoculated to 500 ml. of a liquid incubation medium comprising 1.0% sucrose and 3.0% soybean meal (pH 7.0), which was then shake-cultivated at 28° C for 24 hours. The inculum so obtained was then inoculated to 20 l. of the incubation medium of the same composition which was subsequently incubated under aeration and stirring for 20 hours to prepare a seed culture. This seed culture was inoculated to 200 l. of an aqueous culture medium comprising 1.5% glycerine, 1.5% dextrin, 2.0% soybean meal, 0.15% calcium carbonate and 0.05% sodium thiosulfate (pH 7.0). The inoculated culture medium was incubated at 28° C under aeration and agitation (using a tank-fermentor of 300 l. capacity). 24 Hours and 48 hours after the beginning of the incubation, a sterile aqueous solution of 25% of sodium thiosulfate was added at a rate of 0.15% and 0.2% by weight, respectively, to the incubated culture medium. After 72 hours of the incubation, the resulting culture broth was filtered to give 155 l. of the culture broth filtrate (potency 80 mcg/ml).

The broth filtrate (pH 8.0) was passed through a column of 15 l. of a synthetic adsorber (Amberlite XAD-2, a product of Rhom & Haas Co., U.S.A.) to decolorize the filtrate. The effluent (150 l.) from the column was then passed through a column of 7 l. of an anion-exchange resin (Amberlite IRA- 68 of Cl-cycle) so that the active component, that is, the SF-1623 substance was adsorbed by the anion-exchange resin. The resin column was washed with water and then eluted with 0.5 M aqueous sodium chloride. The first running (5 l.) of the eluate was discarded and the next running (25 l.) was transferred to pass through a column of 2.5 l. of active carbon, so that the active component was adsorbed by the active carbon. The active carbon column was eluted with water and the de-salted aqueous eluate (10 l.) from the carbon column was then passed through a column of 500 ml. of DEAE-Sephadex A-25 (Cl-cycle) (a product of Pharmacia Co., Sweden, an anion-exchange molecular sieve) so that the SF-1623 substance (the sodium salt) was adsorbed by the column of the DEAE-Sephadex A-25. After this column was washed with water, the elution was made with 0.1 M aqueous sodium chloride and the eluate was collected in 20 ml. fractions. The active fractions (the fraction Nos. 71 to 180) were combined together (amounting to 2.2 l. in total), and the combined solution was concentrated to dryness under a reduced pressure to yield 42 g of a crude powder (potency 280 meg/mg) of the SF-1623 substance (in the sodium salt form.

This crude powder (1.2 g) was dissolved in 3 ml. of water and the resulting solution was passed through a column of 50 ml. of DEAE-Sephadex A-25 (Cl-cycle), which column was then washed with 250 ml. of water and subsequently eluted with 0.05 M aqueous sodium chloride. The eluate was collected in 15 ml. fractions. The fraction Nos. 74 to 109 were combined together (amounting to 600 ml. in total), and the combined solution was passed through a column of 60 ml. of active carbon, so that the active substance was adsorbed by the active carbon. The carbon column was washed with water and then eluted with 500 ml. of 60% aqueous acetone (that is, water containing 60% by volume of acetone). The eluate was concentrated under a reduced pressure, affording a colorless powder of the sodium salt of the SF-1623 substance in a yield of 310 mg.

EXAMPLE 2

The crude powder (1.5 g) of the SF-1623 substance (the sodium salt) obtained in Example 1 was taken up into 4 ml. of water, and the resulting aqueous solution was passed through a column of 300 ml. of Sephadex G-10 (a product of Pharmacia Co., Sweden, a molecular sieve gel). The molecular-sieve column was then eluted with water and the eluate collected in 10 ml. fractions. Each of the active fractions was tested by a silica gel thin layer chromatography (using 2:1:1 n-butanol-acetic acid-water as the development solvent). Such active fractions (fractions Nos. 12 to 16) which gave a single spot (as colored by ninhydrin) were combined together, and the combined solution was concentrated to dryness under a reduced pressure. A colorless powder of the sodium salt of the SF-1623 substance was obtained in a yield of 147 mg.

EXAMPLE 3

A loopful amount of spores of *Streptomyces chartreusis* SF-1623 (identified as ATCC 21999) was inoculated to 500 ml. of a liquid medium comprising 1.0% starch and 3.0% soybean meal (pH 7.0), which was then incubated at 25° C for 30 hours under agitation. The resulting culture was employed as the seed culture.

This seed culture was inoculated to 20 l. of a liquid culture medium comprising 2.0% dextrin 1.0% sucrose, 2.0% soybean meal, 0.5% corn steep liquor, 0.15% calcium carbonate, 0.05% di-potassium phosphate and 0.2% sodium thiosulfate (pH 7.0), and the inoculated culture medium was subjected to the cultivation at 28° C under aeration and agitation (using a jar-fermentor of 30 l. capacity). At the end of 50 hours of the cultivation, a sterile aqueous solution of 25% sodium thiosulfate was added at a rate of 0.2% by weight to the culture broth. The cultivation was effected for 90 hours in total. After this, the culture broth was filtered and 15 l. of the filtrate (potency 65 meg/ml) was obtained.

The broth filtrate (pH 7.8) so obtained was passed through a column of 1.5 l. of active carbon, so that the active component, that is, the SF-1623 substance (the sodium salt) was adsorbed by the active carbon. The carbon column was washed with water. The first running (1.2 l.) of the aqueous effluent was discarded and the next running (4.5 l.) was transferred to pass through a column of 250 ml. of an anion-exchange resin (Dowex 1 × 2 of Cl-cycle, 50–100 mesh), so that the active component was adsorbed by the resin. The resin column was washed with water and then eluted with 0.5 M aqueous sodium chloride. The eluate was collected in 100 ml. fractions. The fractions Nos. 2 to 10 were combined together, and the combined solution (900 ml.) was de-salted by passing through a column of 90 ml. of active carbon. The aqueous solution coming as the effluent from the carbon column was concentrated to a volume of 50 ml. under a reduced pressure. The resulting concentrate was twice treated chromatographically with DEAE-Sephadex A-25 (Cl-cycle) in the same manner as in Example 1, affording a colorless powder of the sodium salt of the SF-1623 substance in a yield of 390 mg.

EXAMPLE 4

The crude powder (190 mg) of the SF-1623 substance (the sodium salt) obtained in Example 1 was dissolved in water (2 ml.), and passed through a column of Amberlite IR-120 (H+ type) (a product of Rohm and Haas Co., U.S.A.) (1.4 × 3 cm).

The acidic effluents and aqueous washing are combined together and extracted 3 times with n-butanol (each 30 ml.) and the remaining aqueous layer was lyophilized to give 50 mg of a pale yellow powder. This powder was identified as the free acid form of the SF-1623 substance which did not show a clear melting point but decomposed at 75° to 80° C.

EXAMPLE 5

Experiment discribed in Example 3 was repeated using potassium thiosulfate in place of the sodium thiosulfate and potassium chloride in place of the sodium chloride.

Desalting by the active carbon of the 0.5 M potassium chloride eluate from the DEAE Sephadex A-25, followed by evaporation of the solvent gave a pale-yellow powder of the potassium salt of the SF-1623 substance. (Yield 390 mg). This solid was identified as the potassium salt of the formula:

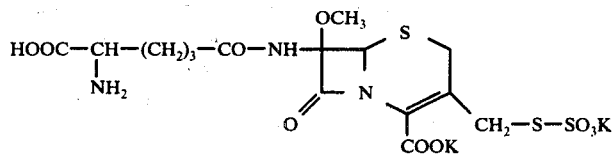

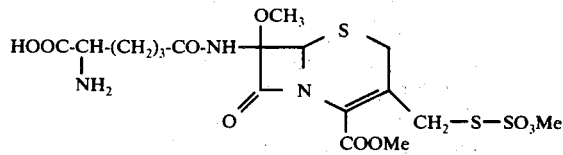

wherein Me is selected from the group consisting of sodium, potassium, and ammonium, which process comprises cultivating an SF-1623 substance-producing strain of *Streptomyces chartreusis* in a culture medium containing assimilable carbon and nitrogen sources under aerobic conditions in the presence of an alkali metal thiosulfate to produce and accumulate the alkali metal salt of the SF-1623 substance in the culture, and then isolating the salt form of this antibiotic from the culture.

2. A process according to Claim 1 in which *Streptomyces chartreusis* SF-1623 (identified as ATCC 21999) is employed as the SF-1623 substance-producing strain.

3. A process according to claim 1 in which the cultivation is carried out at a temperature of 20° to 37° C for a period of 2 to 6 days.

4. A process according to claim 1 in which the cultivation of the SF-1623 substance-producing strain is carried out in the presence of sodium thiosulfate, whereby the SF-1623 substance in the form of its sodium salt is produced and recovered from the culture.

This solid was decomposed in a temperature range of 170° to 175° C.

The preceding examples can be repeated with similar success by substituting the generically or specifically described reactants and/or operating conditions of this invention for these used in the preceding example.

From the foregoing description, one skilled in the art can easily ascertain the essential characteristics of this invention, and without departing from the spirit and scope thereof, can make various changes and modifications of the invention to adapt it to various usages conditions.

What we claim is:

1. A process for the production of an alkali metal salt of SF-1623 substance having the formula:

* * * * *